May 9, 1972 W. E. LAMMERTS Plant Pat. 3,162

ROSE PLANT

Filed Sept. 25, 1970

INVENTOR.
WALTER E. LAMMERTS

BY Rummler & Snow
Attys

United States Patent Office

Plant Pat. 3,162
Patented May 9, 1972

3,162
ROSE PLANT

Walter E. Lammerts, Freedom, Calif., assignor to Germain's Inc., Los Angeles, Calif.

Filed Sept. 25, 1970, Ser. No. 75,794
Int. Cl. A01h *5/00*
U.S. Cl. Plt.—22 1 Claim

ABSTRACT OF THE DISCLOSURE

A new floribunda variety of rose plant particularly characterized by the very clear and uniform red margin extending completely around each petal, except for the base, which in the opening stage of the bloom contrasts sharply with the basic ivory color of the rest of the petal. The new plant is a free producing variety and under greenhouse conditions produces blooms throughout the entire year that have excellent lasting quality as cut flowers.

BACKGROUND OF THE INVENTION

My new variety of rose plant resulted from breeding efforts carried on by me at Livermore, Calif., since 1953 with the object of obtaining a floribunda variety that would approximate the delicate coloring of Peace (P.P. 591) and at the same time maintain hybrid vigor and productiveness. This was accomplished by crossing Peace with the wholly unrelated variety Rumba (P.P. 1,919) and in 1963 the present new variety was discovered among seedlings so produced. The new plant, in addition to the distinctively novel coloring of its blooms, was found to have the vigor and productiveness of Rumba, as well as the firm glossy foliage of both parent varieties, and asexual propagation of this plant at Livermore, Calif., by budding, has shown these advantages to be firmly fixed and to hold true from generation to generation.

Propagation of this new variety of rose plant is now being carried on at Livermore, Calif.; at Hamilton City, Calif.; and at Phoenix, Ariz. The following specification, however, is based upon observations made under greenhouse conditions at Livermore, Calif., and at Salinas, Calif., and under nursery field conditions at Hamilton City, Calif.

DESCRIPTION OF THE DRAWINGS

My new variety of rose plant is illustrated by the accompanying photographic representation in which the upper view shows the flower in various stages of development from bud, when calyx splits, to fully opened bloom; and the lower view shows front and back sides of typical leaves, portions of young and mature wood, and a flowering stem with a new bud.

DESCRIPTION OF THE NEW PLANT

Figure 1:
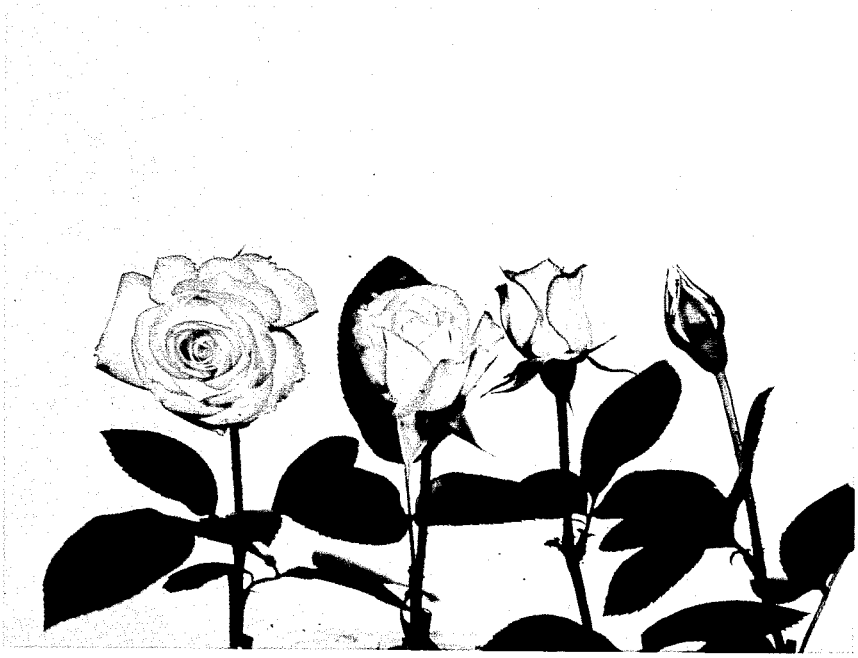
Figure 2:
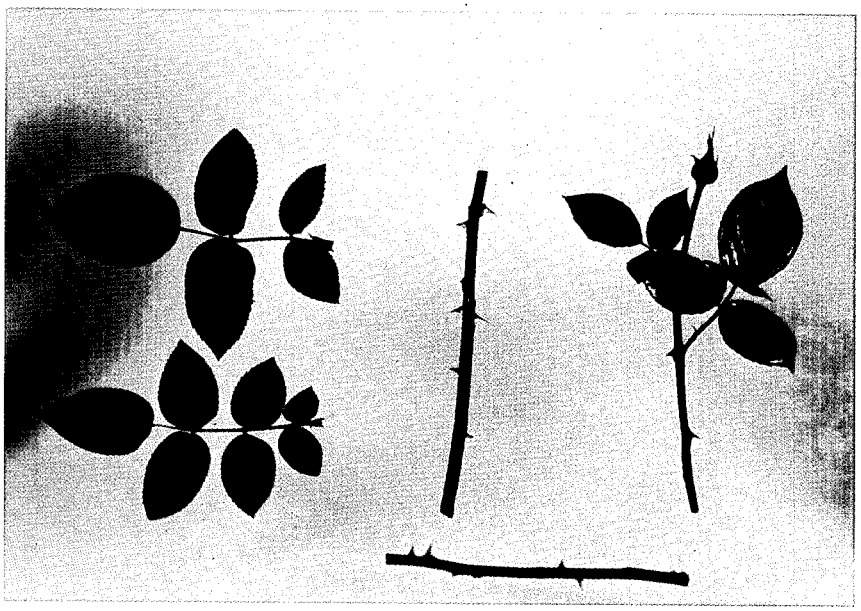

The following is a detailed description of the new floribunda variety of rose plant with color designations according to the R.H.S. Colour Chart of the Royal Horticultural Society at London, England.

*The plant*

Origin: Seedling.
Parentage:
*Seed parent.*—Peace (Plant Patent 591).
*Pollen parent.*—Rumba (Plant Patent 1,919).
Classification:
*Botanic.*—Floribunda.
*Commercial.*—Hothouse rose.

Form: Compact, rounded bush.
Height: 5 to 6 feet in greenhouse; 2 to 3 feet in garden.
Growth: Full and moderately vigorous; sturdy and semi-upright with firm canes and stems; and very free branching.
Foliage: Quantity—abundant, with many leaves spaced 1½ to 2½ inches apart on flowering stem.
*Leaf size.*—Medium 3½ to 5½ inches long—Shape—Odd pinnate
*Leaflet size.*—1⅛ to 1½ inches wide by 1⅝ to 2¾ inches long—Number—3 to 7, mostly 5—Color—upper side—Green 137A—under side—Greyed-Green 191A — texture—Leathery—appearance—glossy — serrated — pronounced and uniform—petioles—1/16 to ⅛ inch long—ribs and veins—prominent, on both sides of leaflets.
*Rachis.*—Stipules are adnate. There are small hairs tipped with glands around the edge of the stipules and the auricles are slender. The under side of the rachis has 3 to 7 hooked thorns ⅛ to 3/16 inch long.
*Thorns/spines.* — Color — Greyed-Orange 165B—size—base to point—⅛ to ⅜ inch—length of base—⅛ to 9/16 inch—width of base—1/32 to 5/32 inch.
*Prickles.*—Interspersed with thorns on both peduncle and rachis. Not on any other part of plant.

*The bud*

Form: Ovoid and pointed.
Size: When sepals first divide—1 to 1⅛ inches wide at base by 1⅛ to 1¼ inches long. When one-quarter open—diameter 1⅛ to 1¼ inches at base by 1¼ to 1⅜ inches deep.
Opening: Bud opens slowly.
Color: When sepals first divide—Red-Purple 60A margins; visible balance Yellow-White 158A. When sepals begin to unfurl—outside petal, White 155D with Red-Purple 57C margins.
Sepals: Hooded over bud.
*Form.*—Spear shaped with minute hairs of White 155D color, at the margins; and having random slender marginal lacinations. Sepals curl back as petals open.
*Color.*—Inside—Green 138B near margin to Green 138D—outside —Green 138B.
Calyx:
*Shape.*—Pear shaped.
*Size.*—Large, ⅝ to ¾ inch broad by ½ inch long.
*Aspect.*—Smooth at base.
Peduncle: Sturdy and erect; 2 to 2½ inches long; with many small prickles except for top ¼ to ⅜ inch which is smooth.
Color—Yellow-Green 152B.

*The flower*

Blooming habit: Continuous and profusely from early spring through late fall; also blooms through winter when under glass.
Size: Medium, 3 to 3½ inches in diameter, 1¼ to 1½ inches deep.
Borne: Singly and in clusters of 2 to 4 blooms.
Shape: When bloom first opens—high center form changes later to globular imbricated.
Petalage: Number—37 to 42,
*Arrangement.*—Imbricated, petaloids hide pistils and stamens.

*Color.*—Outer petals—Main color, White 155B. Margin, Red-Purple 57B. Inside petals—Main color, Yellow 11D. Margin, Red-Purple 57D. Reverse sides of petals same colors as the top sides and both sides of the petals have a faint mid-rib and veins of Yellow-Green 145C color. Petal base—Greyed-Yellow 160A.

*Texture.*—Firm, with midly velvety appearance.

Petaloids: Number—18 to 22,

*Size.*—⅛ to ⅝ inch by ⅜ to ¾ inch.

*Color.*—Margin—Red - Purple 73C—Main color—Yellow 11D—Base—Yellow-Orange 14C.

Peduncle: Sturdy and upright; 2 to 2¼ inches long; and Yellow-Green 152B in color.

Discoloration: Colors blend together after full bloom.

Persistence: Flowers hang on and drop cleanly without drying on plant. Petals stay on stem for 18 to 22 days.

Disease Resistance: Plant resists mildew and rust as observed in growing areas where these diseases are present.

Fragrance: Blooms have a slight undefinable fragrance.

Lasting quality: 18 to 22 days on plant; 8 to 9 days as a cut flower.

*Reproductive organs*

Stamens:

*Anthers.*—Introrse arrangement; 1/16–3/16 inch long; and 189 to 192 in number.

*Filaments.*—1/32 to 5/32 inch long. Color—Yellow 9C.

Pollen: Color—Yellow-Orange 17B.

Pistils: ⅜ to 7/16 inch long; 154 to 171 in number.

Stigmas: Color—Yellow 5C.

Ovaries: Covered with fine hairs, styles are unattached to each other throughout.

*Fruit*

Fruit is fertile and of round shape.

Color at maturity is Orange-Red 30C.

The principal and outstanding distinction of my new variety of rose plant over any other fluoribunda varieties resides in the very clear and substantially uniform red margin which extends around the entire periphery of each petal, except for the base. In the opening stages of the bloom this margin contrasts very sharply with the basic ivory color of the rest of the petal, providing a very distinctive and pleasing appearance.

Another distinctive characteristic of the new variety is the coloring of the bark which turns to a reddish-brown as the bloom matures, but only in that portion or area exposed to direct sunlight. Any shaded portion, no matter how small, retains the original green color.

The variety of rose plant most nearly resembled by my new variety is Peppermint (P.P. 2549). My new variety, however, is distinguished from Peppermint by the clear band of color at the margin of the petals whereas Peppermint has a diffusion of colors. Furthermore, my new variety has much more of the basic ivory color in its bloom and more yellow on the inside petals; a more glossy foliage than Peppermint; and a more compact and shorter growing habit.

A particular advantage of my new rose plant is that it is a free producing fluoribunda variety that produces blooms throughout the entire year under greenhouse conditions and the number and texture of the petals affords excellent lasting quality to the blooms as cut flowers. Also, the plant foliage is outstanding both as to quantity and appearance.

I claim:

1. A new and distinctive variety of fluoribunda rose plant substantially as herein shown and described, characterized by the generally uniform red margin extending along the entire edge of each petal of the blooms and contrasting sharply with the basic generally ivory color of the petal body; and in the reddish-brown coloration of the bark which occurs only in the portions exposed to direct sunlight as the bloom matures.

No references cited.

ROBERT E. BAGWILL, Primary Examiner